United States Patent
Chen et al.

(10) Patent No.: US 10,176,572 B2
(45) Date of Patent: Jan. 8, 2019

(54) METHOD ADAPTED TO DIAGNOSE AIRWAY OBSTRUCTION AND SYSTEM THEREOF

(71) Applicant: AmCad BioMed Corporation, Taipei (TW)

(72) Inventors: Argon Chen, Taipei (TW); Yi-li Lee, Taipei (TW); Chun-Hsiang Yang, Taipei (TW); Edward Chia-Hao Liu, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 55 days.

(21) Appl. No.: 15/395,434

(22) Filed: Dec. 30, 2016

(65) Prior Publication Data

US 2017/0365052 A1 Dec. 21, 2017

(30) Foreign Application Priority Data

Jun. 15, 2016 (TW) .............................. 105118785 A

(51) Int. Cl.
*G06T 7/00* (2017.01)
*G06T 7/11* (2017.01)
(Continued)

(52) U.S. Cl.
CPC .............. *G06T 7/0012* (2013.01); *A61B 8/08* (2013.01); *A61B 8/5223* (2013.01); *G06T 7/11* (2017.01);
(Continued)

(58) Field of Classification Search
CPC .................... G06T 7/0012; G06T 2207/10132
See application file for complete search history.

(56) References Cited

U.S. PATENT DOCUMENTS 9,153,022 B2 * 10/2015 Finkelstein .......... A61B 5/1075
2011/0152965 A1 * 6/2011 Mashiach ............ A61B 5/0031
607/42

(Continued)

OTHER PUBLICATIONS

Shu et al. "The Use of Sub-Mental Ultrasonography for Identifying Patients with Severe Obstructive Sleep Apnea", May 2013, PLOS ONE, vol. 8, issue 5, e62848.*

(Continued)

*Primary Examiner* — Qian Yang
(74) *Attorney, Agent, or Firm* — Birch, Stewart, Kolasch & Birch, LLP

(57) ABSTRACT

A method adapted to diagnose airway obstruction in a subject is disclosed. The method comprises the following steps: providing plural cross-sectional ultrasound images of a region of the respiratory tract during the subject's normal breathing, wherein each ultrasound image has plural pixels and each pixel has a color scale value; selecting a region of interest in each ultrasound image; calculating a respective first statistic value. The pixels in each of the region of interest are identified to define a respective airspace region by the color scale values larger than or equal to the respective first statistic value. A respective width of the respiratory tract is calculated and based on the distribution of the pixels in the respective airspace region. The status about an airway obstruction in the subject is classified according to the second statistic value obtained by the calculation of the widths of the respiratory tract.

5 Claims, 9 Drawing Sheets

(51) Int. Cl.
    *G06T 7/90*          (2017.01)
    *A61B 8/08*        (2006.01)
    *A61B 8/00*        (2006.01)
    *G06T 7/136*       (2017.01)

(52) U.S. Cl.
    CPC .............. *G06T 7/90* (2017.01); *A61B 8/4461* (2013.01); *A61B 8/4483* (2013.01); *A61B 8/483* (2013.01); *G06T 7/136* (2017.01); *G06T 2207/10132* (2013.01)

(56) References Cited

U.S. PATENT DOCUMENTS

| | | | | |
|---|---|---|---|---|
| 2013/0004044 A1* | 1/2013 | Ross | ............... | G06T 7/0016 382/131 |
| 2013/0217996 A1* | 8/2013 | Finkelstein | .......... | A61B 5/1075 600/407 |
| 2013/0289401 A1* | 10/2013 | Colbaugh | ............ | A61B 5/0488 600/437 |
| 2015/0209001 A1* | 7/2015 | Wolf | ............... | A61B 8/085 600/301 |
| 2016/0029927 A1* | 2/2016 | Finkelstein | .......... | A61B 5/1075 382/132 |

OTHER PUBLICATIONS

Al-Abed et al. "Upper Airway Occlusion Detection Using a Novel Ultrasound Technique", 34th Annual International Conference of the IEEE EMBS San Diego, California USA, Aug. 28-Sep. 1, 2012.*

\* cited by examiner

METHOD ADAPTED TO DIAGNOSE AIRWAY OBSTRUCTION AND SYSTEM THEREOF

FIELD OF THE INVENTION

The disclosure relates to a method adapted to diagnose airway obstruction in a subject and a system thereof. More particularly, the disclosure relates to computer-implemented method for determining a width of a respiratory tract and a system thereof.

BACKGROUND OF THE INVENTION

Sleep apnea is a chronic sleep disorder that happens when a person stops breathing during sleep. Sleep apnea is most commonly diagnosed in middle aged males. It is estimated that about one in 20 adults has been identified with sleep apnea, and is about 2 to 8 times more common among men than among women. Recent studies have shown that the prevalence of childhood sleep apnea is much higher than we expected. In addition, obesity, enlarged tonsil tissues, nasal septum deviation, alcohol intake, smoking and sedative use are related to a high risk for sleep apnea.

The standard diagnostic tools for sleep apnea are overnight polysomnogram and overnight oximetry. A well-known evaluation method of an apnea includes a minimum 10 second interval between breaths, or a hypopnea in which airflow decreases by 50 percent for 10 seconds. The evaluation process is time consuming and labor intensive. Moreover, qualified staff is unable to measure polysomnogram values accurately with a standardized evaluation procedure.

In prior art, a 2D ultrasonic sensing device is used for diagnosing airway obstruction. However, the 2D ultrasonic sensing device is limited by the relative position between cross-sectional surfaces and a respiratory tract, such that regions of the respiratory tract cannot be positioned accurately. Additionally, when different operators use the 2D ultrasonic sensing device to scan the same region of the respiratory tract at different time, it may produce different results from different positions and different sectioning angles.

SUMMARY OF THE INVENTION

The disclosure provides a computer-implemented method for determining a width of a respiratory tract and system thereof. More particularly, the disclosure relates to method for diagnosing airway obstruction and system thereof, based on determining the width of the respiratory tract.

One aspect of the disclosure provides a computer-implemented method for determining a width of a respiratory tract, which comprises the following steps. An ultrasound image of a region the respiratory tract is provided. The ultrasound image has a plurality of pixels, and each pixel has a color scale value. A region of interest in the ultrasound image is selected. A first statistic value of color scale value of the pixels therein is calculated. The pixels in the region of interest are identified and have a color scale value larger than or equal to the first statistic value, to define an airspace region. The width of the respiratory tract is calculated and based on the distribution of the pixels in the airspace region.

In another aspect, the disclosure provides a system for determining a width of a respiratory tract. The system comprises an ultrasound imaging device and a computing device. The computing device comprises an input module, a classifier module and an output module. The ultrasound imaging device is used for collecting an ultrasound image of a region of a respiratory tract. The ultrasound image has a plurality of pixels, and each pixel has a color scale value.

The computing device is coupled to the ultrasound imaging device. The input module is used for receiving the ultrasound image. A user is allowed to input a command to select region of interest. Additionally, the input module is used for calculating a respective first statistic value of the color scale values of the pixels. The classifier module is used for identifying the pixels in the region of interest which have a color scale value larger than or equal to the first statistic value, to define an airspace region. Additionally, the classifier module is for calculating a width of the respiratory tract based on the distribution of the pixels in the airspace region. The output module is used for outputting the width of the respiratory tract and displaying the ultrasound image.

In another aspect, the disclosure provides a method adapted to diagnose airway obstruction in a subject in need thereof, which comprises the following steps. A plurality of cross-sectional ultrasound images of a region of the respiratory tract during the subject's normal breathing are provided. Each ultrasound image has a plurality of pixels, and each pixel has a color scale value. A region of interest is selected in each ultrasound image, and a respective first statistic value of color scale value of the pixels therein is calculated. The pixels in each the region of interest are identified and have a color scale value larger than or equal to the respective first statistic value to define a respective airspace region. A respective width of the respiratory tract is calculated and based on the distribution of the pixels in the respective airspace region. A second statistic value of the widths of the respiratory tract is calculated. The status about an airway obstruction in the subject is classified according to the second statistic value In another aspect, the disclosure provides a system adapted to diagnose airway obstruction in a subject in need thereof, which comprises an ultrasound imaging device, a first computing device, a second computing device and an identifying device. The ultrasound imaging device is adapted to collect an ultrasound image of a region of the respiratory tract. The ultrasound image has a plurality of pixels, and each pixel has a color scale value.

The first computing device is coupled to the ultrasound imaging device which comprises an input module, a classifier module and an output module. The input module is for receiving the ultrasound image and allowing a user to select a region of interest. A respective first statistic value of color scale value of the pixels therein is calculated. The classifier module is for identifying pixels in the region of interest which have a color scale value larger than or equal to the respective first statistic value to define a respective airspace region. Additionally, the classifier module is for calculating a respective width of the respiratory tract based on the distribution of the pixels in the respective airspace region. The output module is for outputting the respective width of the respiratory tract and displaying the ultrasound image.

The second computing device is coupled to the first computing device, for calculating a second statistic value of the widths of the respiratory tract. The identifying device is coupled to the second computing device and adapted to classify the status about an airway obstruction in the subject.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Unless defined otherwise, all technical and scientific terms used herein have the same meaning as commonly understood by a person skilled in the art to which this invention belongs.

As used herein, the singular form's "a", "an", and "the" include plural referents unless the context clearly dictates otherwise. Thus, for example, reference to "a sample" includes a plurality of such samples and equivalents thereof known to those skilled in the art.

As used herein the term "Measure of Location (ML)" refers to an average value of an interval value. It is an appropriate value which represents whole data of the interval, which may be an arithmetic mean value, a statistical percentile value, a geometric mean value, a harmonic mean value, a median value, a mode value, a weighted arithmetic mean or other measures used for representing a value of central tendency. According to the embodiment of the present invention, ML is a value selected from the group consisting of a mode value, a statistical percentile value, an average value and other measures used for representing value of central tendency.

The term "Measure of Dispersion (MD)" as used herein refers to a statistical characteristic which denotes the extent of distribution set of data. It is also called "dispersion". MD is categorized into a dispersion variation and a non-dispersion variation. According to the embodiment of the present invention, MD is a value selected from the group consisting of a standard deviation, a whole range and other measures used for representing value of central dispersion.

The disclosure provides a computer-implemented method for determining a width of a respiratory tract and a method adapted to diagnose airway obstruction in a subject in need thereof. The methods are applied to an ultrasonic sensing device. Moreover, the methods are applied to a computer or a microprocessor which is connected to the ultrasonic sensing devices for collecting and saving image data. Additionally, the methods are programmable and saved in a recording media with micro processing unit, or a device with the recording media. The device is, but not limited to, a hard disc, floppy disc, a compact disc, a magneto-optical device, an integrated circuit (IC) chip, or a random access memory.

Figure 1:
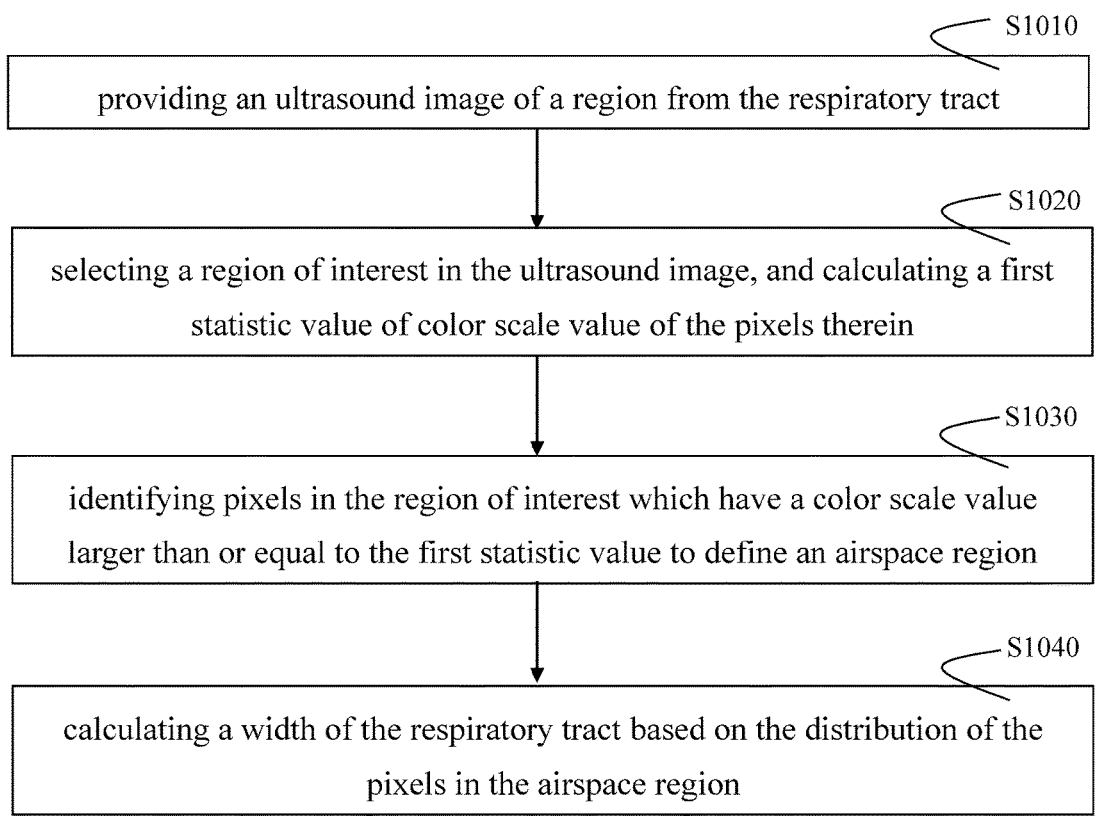
FIG. 1 is a flow diagram of a computer-implemented method for determining a width of a respiratory tract.

Please refer to FIG. 1 the computer-implemented method for determining the width of the respiratory tract comprises the following steps. First, as shown in step S1010, an ultrasound image of a region the respiratory tract is provided. The ultrasound image has a plurality of pixels, and each pixel having a color scale value. Then, as shown in step S1020, a region of interest in the ultrasound image is selected. A first statistic value of color scale value of the pixels therein is calculated. Then, as shown in step S1030, the pixels in the region of interest are identified and have a color scale value larger than or equal to the first statistic value, to define an airspace region. Finally, as shown in step S1040, the width of the respiratory tract is calculated and based on the distribution of the pixels in the airspace region.

Figure 2A:
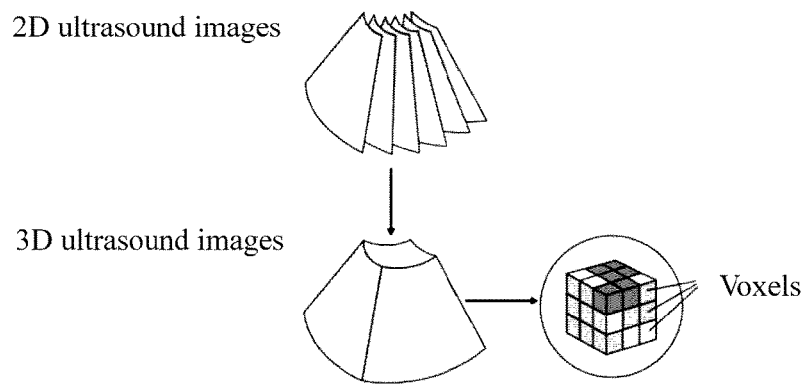
FIG. 2A through FIG. 2C are a plurality of cross-sectional images captured from a retro-glossal region or retro-palatal region of a respiratory tract from a plurality of respective sectioning angles by an ultrasound imaging device according to an embodiment.
Figure 2B:
Figure 2C:
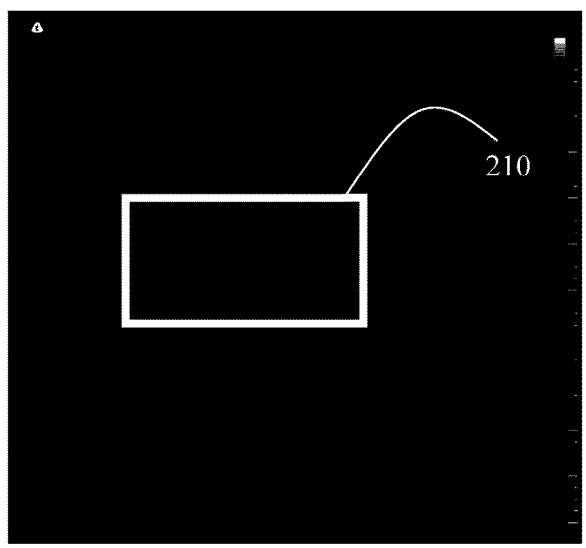

Referring to FIG. 2A through FIG. 2C showing one embodiment of the invention, the ultrasound images are a plurality of cross-sectional images of said region of the respiratory tract from a plurality of respective sectioning angles (see FIG. 2A). Additionally, a 2D ultrasonic probe can be used in different ways, such as parallel scanning, fan-like scanning, or free-surface scanning etc., to obtain 2D ultrasound images. Each ultrasound image has a plurality of pixels, and each pixel is analyzed. In some embodiments, the ultrasound image can be a 3D ultrasound image formed by the 2D ultrasound images. The ultrasound image has a plurality of voxels, and each voxel is analyzed.

As shown in FIG. 2B, a retro-glossal region or a retro-palatal region of the respiratory tract is scanned by an ultrasonic sensing device, to obtain the ultrasound images which are the cross-sectional images of said region of the respiratory tract from the respective sectioning angle. Furthermore, each pixel has a gray scale.

As shown in FIG. 2C, a region of interest 210 is selected in the ultrasound image. The gray scales of the pixels are calculated, to define an airspace region by identifying pixels in the region of interest 210 which have a color scale value larger than or equal to the first statistic value. Finally, a width of the respiratory tract is defined as a farthest distance of any two pixels in the airspace region according to an embodiment of the invention.

In a specific embodiment of the invention, the first statistic value is a sum of a measure of location (ML) of the color scale values plus a constant multiplied by a measure of dispersion (MD). Namely, the first statistic value satisfies the following condition:

$$ML+a*MD.$$

The MD is selected from the group consisting of a standard deviation, a whole range and other dispersion values. The ML is selected from the group consisting of a mode value, a statistical percentile value, an average value or other location dispersion. The constant a is, but not limited to, a positive number, and representing a value of central dispersion, which is selected by medical personnel.

Figure 3:
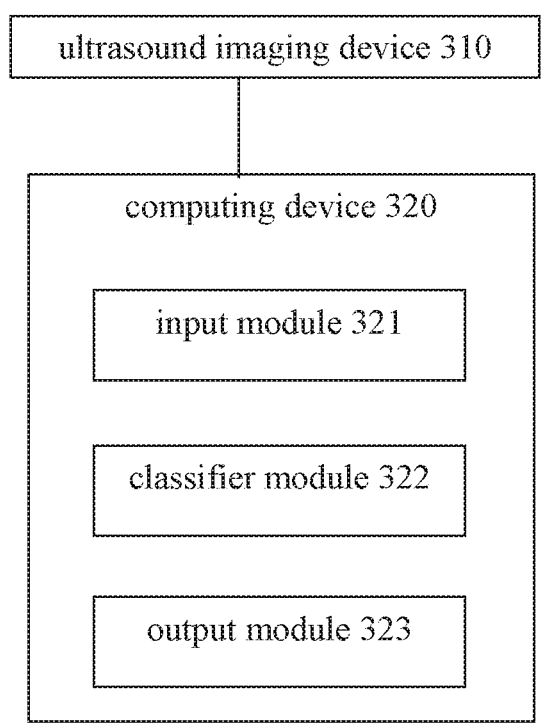
FIG. 3 is a schematic view of a system for determining a width of a respiratory tract.

Please refer to FIG. 3. A system is provided to accomplish the computer-implemented method. The system comprises an ultrasound imaging device 310 and a computing device 320. The ultrasound imaging device 310 is used for collecting an ultrasound image of a region of a respiratory tract.

The ultrasound image has a plurality of pixels, and each pixel has a color scale value. In one embodiment, the ultrasound imaging device 310 is, but not limited to, a 2D ultrasonic probe or a 3D ultrasonic probe. Preferably, the ultrasound imaging device 310 is a 2D ultrasonic probe, and the ultrasound image is obtained by parallel scanning, fan-like scanning or free-surface scanning.

The computing device 320 is coupled to the ultrasound imaging device 310. Furthermore, the ultrasound imaging device 310 comprises an input module 321, a classifier module 322 and an output module 323. In one embodiment, the computing device 320 is, but not limited to, a computer or a handheld device. Preferably, the computing device 320 is a computer with a memory and a central processing unit (CPU). A proper program is installed in the memory to operate the computer-implemented method with the CPU.

The input module 321 of the computing device 320 is used for receiving the ultrasound image. A user is allowed to input a command to select a region of interest. Additionally, the input module 321 is used for calculating a respective first statistic value of the color scale values of the pixels. In one embodiment, the input module 321 is a signal input terminal of the computing device 320. The input module 321 is wiredly or wirelessly connected to the ultrasound imaging device 310. For example, the input module 321 is, but not limited to, a touch screen or a mouse.

The classifier module 322 is used for identifying the pixels in the region of interest which have a color scale value larger than or equal to the first statistic value, to define an airspace region. Additionally, the classifier module 322 is for calculating a width of the respiratory tract based on the distribution of the pixels in the airspace region. In one embodiment, the classifier module 322 is, but not limited to, a CPU.

The output module 323 is used for outputting the width of the respiratory tract and displaying the ultrasound image. The ultrasound image has the region of interest, the airspace region and a non-airspace region. In one embodiment, the output module 323 is a signal output terminal of the computing device 320 and wiredly or wirelessly connected to a storage device or an output interface. For example, the output module 323 is, but not limited to, a touch screen.

Figure 4:
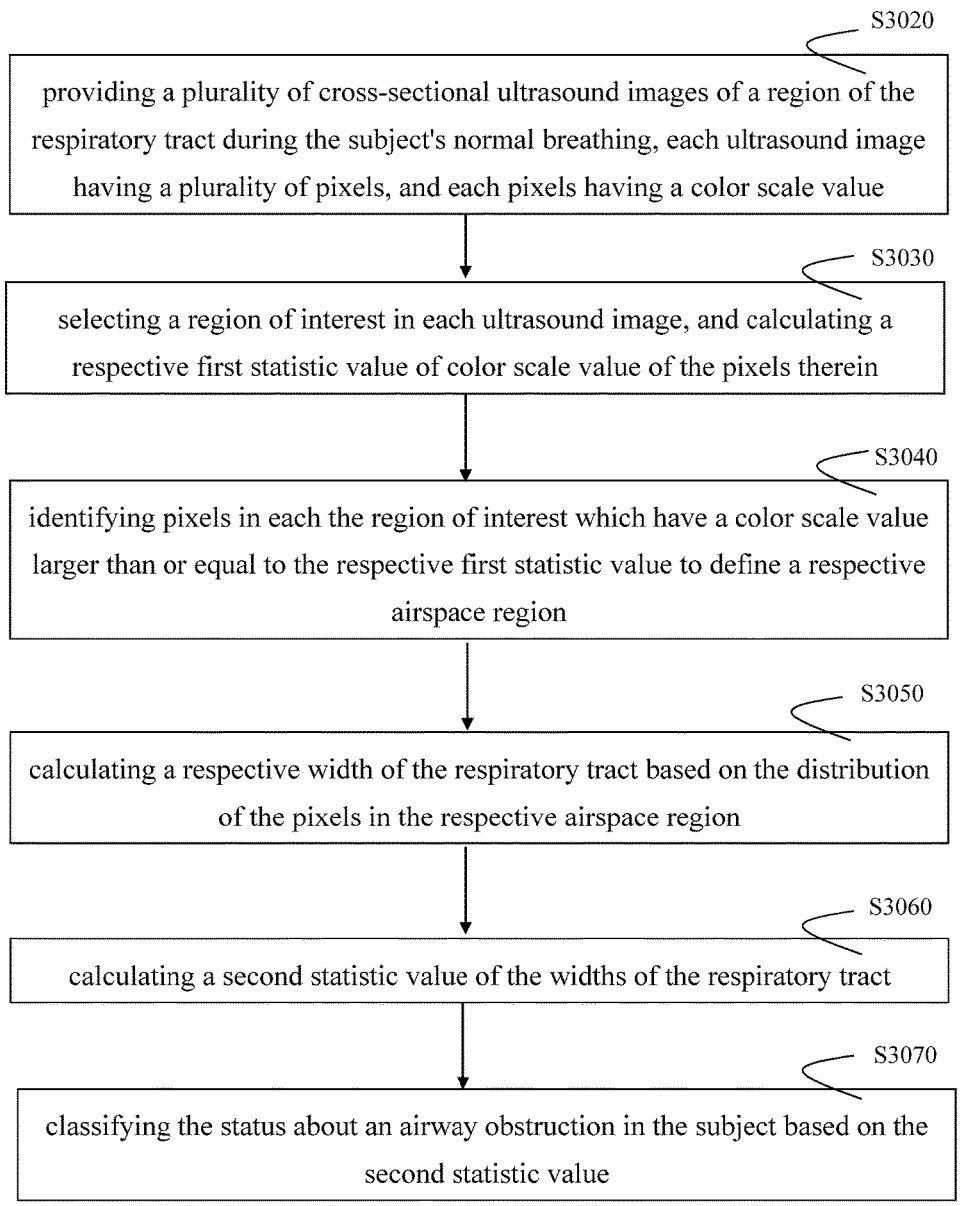
FIG. 4 is a flow diagram of A method adapted to diagnose airway obstruction in a subject.

Please refer to FIG. 4 which is a flow diagram of a method adapted to diagnose airway obstruction in a subject. The method comprises the following steps. First, as shown in step S3020, a plurality of cross-sectional ultrasound images of a region of the respiratory tract during the subject's normal breathing are provided. Each ultrasound image has a plurality of pixels, and each pixel has a color scale value. As shown in step S3030, a region of interest is selected in each ultrasound image, and a respective first statistic value of color scale value of the pixels therein is calculated. As shown in step S3040, the pixels in each the region of interest are identified and have a color scale value larger than or equal to the respective first statistic value to define a respective airspace region. As shown in step S3050, a respective width of the respiratory tract is calculated and based on the distribution of the pixels in the respective airspace region. As shown in step S3060, a second statistic value of the widths of the respiratory tract is calculated. Finally, as shown in step S3070, the status about an airway obstruction in the subject is classified according to the second statistic value.

Additionally, the method for diagnosing airway obstruction comprises the following step. A third statistic value is obtained by repeating the steps S3020 through S3060 during the subject is asked to breathe in a specific manner. Whether the subject has an airway obstruction or not is determined by comparing the second statistic value and the third statistic value determines.

Figure 5:
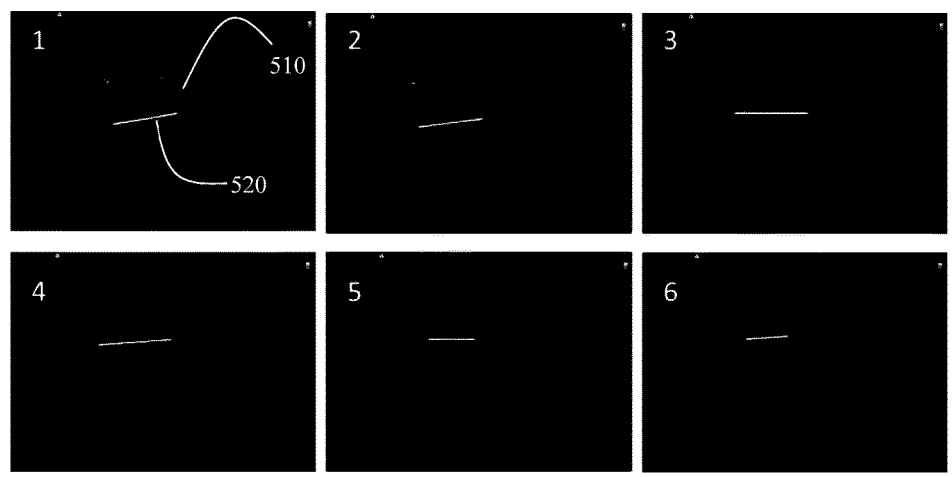
FIG. 5 illustrates a plurality of ultrasound images during a subject who is asked to breathe normally according to an embodiment.

Please refer to FIG. 5. In one embodiment, the subject is asked to breathe normally. A retro-glossal region or a retro-palatal region of the respiratory tract is scanned by an ultrasonic sensing device to obtain the ultrasound image which is a plurality of cross-sectional images of said region of the respiratory tract from a plurality of respective sectioning angles. Furthermore, each pixel has a gray scale. Then, a region of interest 510 is selected from the ultrasound images respectively. The gray scales of the pixels are calculated, to define a respective airspace region by identifying pixels in the region of interest 510 which has a color scale value larger than or equal to the respective first statistic value. Then, a width 520 of the respiratory tract is defined as a farthest distance of any two pixels in the respective airspace region. A second statistic value of the widths of the respiratory tract is calculated, which is a maximum value, a minimum value and a measure of a percentage value.

Figure 6:
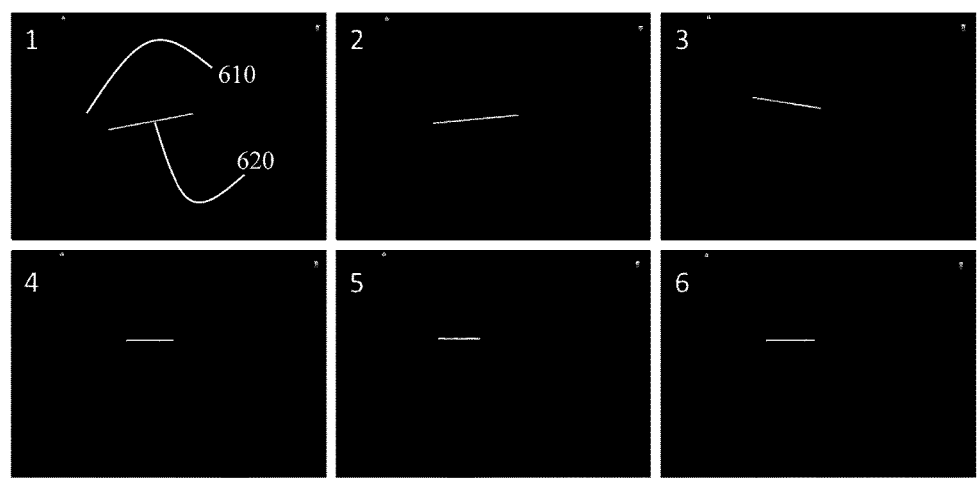
FIG. 6 illustrates a plurality of ultrasound images captured from a cross-sectional images of respiratory tract during a subject who is asked to breathe in a specific manner according to an embodiment.

Similarly, as shown in FIG. 6, the subject is asked to breathe in a specific manner. A retro-glossal region or a retro-palatal region of the respiratory tract is scanned by an ultrasonic device, to obtain the ultrasound image which is a plurality of cross-sectional images of said region of the respiratory tract from a plurality of respective sectioning angles. A region of interest 610 is selected from the ultrasound images. Then, a width 620 of the respiratory tract is defined as a farthest distance of any two pixels in the respective airspace region similarly. In one embodiment, the specific manner is a tidal breathing method, a forced inspiration, or a Muller maneuver.

In one embodiment, the statistic values are obtained by the subject being asked to breathe normally are compared to the statistic values obtained by the subject being asked to breathe in a specific manner, to determine whether the subject has an airway obstruction or not. In a specific embodiment, a second statistic value and a third statistic value are obtained by measuring the width of the respiratory tracts. Then, the compared values are obtained by comparing those two values (e.g. subtracting or dividing those two values) to confirm if the subject has an airway obstruction.

In one embodiment, the ultrasound image is collected by the ultrasound imaging device, and the respective first statistic value is a sum of the ML plus the constant multiplied by the MD. In one embodiment, the ML is an arithmetic mean value of the color scale values in the region of interest, and the constant a is equal to 1. Namely, the respective first statistic value satisfies the following condition:

$$ML+1*MD.$$

Figure 7:
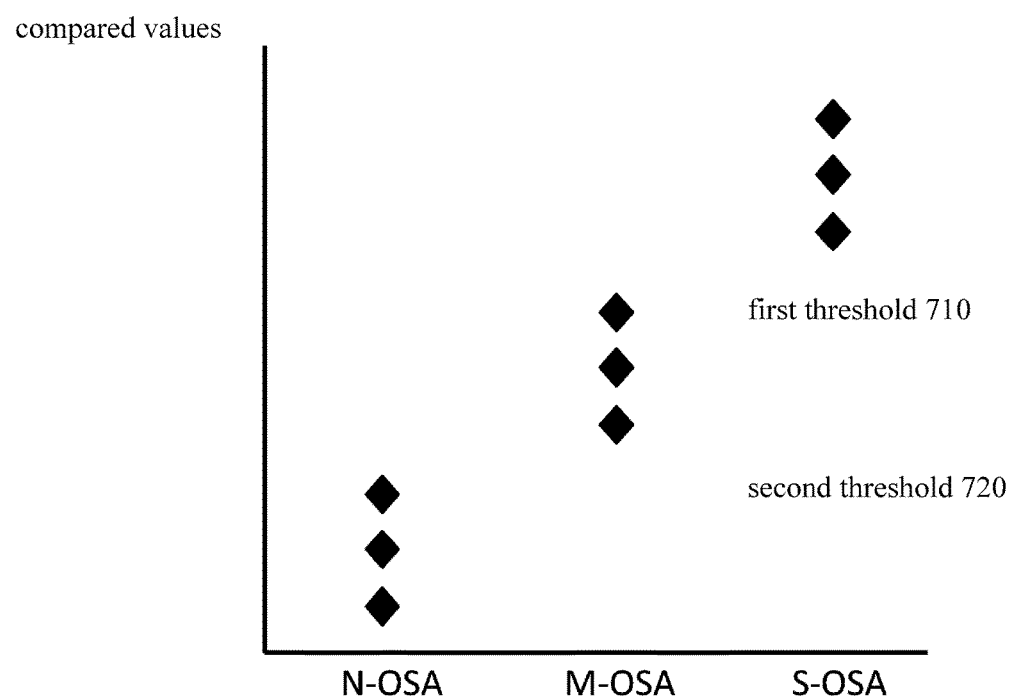
FIG. 7 is a diagram of a plurality of compared values obtained from a patient suffered from obstructive sleep apnea (OSA), such as an S-OSA patient, an M-OSA patient and an N-OSA patient, who are asked to breathe in said specific manner according to the previous embodiment.

Please refer to FIG. 7. In one embodiment, compared values are obtained by asking a Severe Obstructive Sleep Apnea (S-OSA) patient, a Moderate Obstructive Sleep Apnea (M-OSA) patient and a Non Obstructive Sleep Apnea (N-OSA) patient to breathe normally and breathe in a specific manner. As shown in FIG. 7, in light of the distribution of variation from those three widths of the respiratory tracts, the expression level of the OSA patient is lower than that of common people. Particularly, when the statistical values become lower, the airway obstruction of the patients are more serious. Accordingly, the diagram shown in FIG. 7 can be a reference to determine whether the subject has an airway obstruction.

For example, the compared values of the S-OSA patient are larger than a first threshold 710. The compared values of the M-OSA patient are between the first threshold 710 and a second threshold 720. Additionally, the compared values of the N-OSA patient are less than the second threshold 720.

Figure 8:
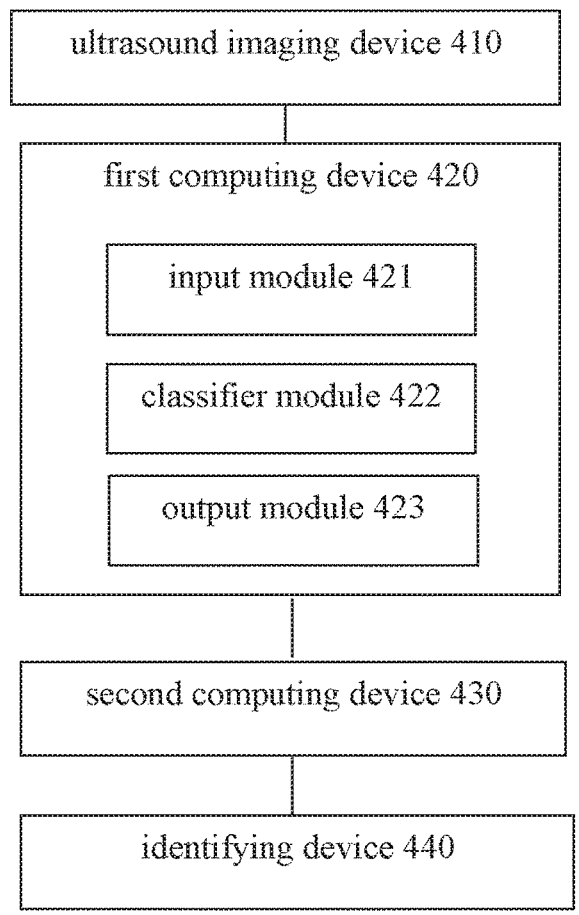
FIG. 8 is a schematic view of a system adapted to diagnose airway obstruction in a subject.

Referring to FIG. 8 providing a system to diagnose airway obstruction in a subject, the system comprises an ultrasound imaging device 410, a first computing device 420, a second computing device 430 and an identifying device 440. The ultrasound imaging device 410 is used for collecting an ultrasound image of a region of a respiratory tract. The ultrasound image has a plurality of pixels, and each pixel has a color scale value. In one embodiment, the ultrasound imaging device 410 is, but not limited to, a 2D ultrasonic probe or a 3D ultrasonic probe. Preferably, the ultrasound imaging device 410 is a 2D ultrasonic probe, and the ultrasound image is obtained by parallel scanning, fan-like scanning or free-surface scanning.

The first computing device 420 is coupled to the ultrasound imaging device 410. Furthermore, the ultrasound imaging device 410 comprises an input module 421, a classifier module 422 and an output module 423. In one embodiment, the first computing device 420 is, but not limited to, a computer or a handheld device. Preferably, the first computing device 420 is a computer with a memory and a central processing unit (CPU). A proper program is installed in the memory to operate the computer-implemented method with the CPU.

The input module 421 of the first computing device 420 is used for receiving the ultrasound image. A user is allowed to input a command to select a region of interest. Additionally, the input module 421 is used for calculating a respective first statistic value of the color scale values of the pixels. In one embodiment, the input module 421 is a signal input terminal of the first computing device 420. The input module 421 is wiredly or wirelessly connected to the ultrasound imaging device 410. For example, the input module 421 is, but not limited to, a touch screen or a mouse.

The classifier module 422 is used for identifying the pixels in the region of interest which have a color scale value larger than or equal to the respective first statistic value, to define a respective airspace region. Additionally, the classifier module 422 is for calculating a respective width of the respiratory tract based on the distribution of the pixels in the respective airspace region. In one embodiment, the classifier module 422 is, but not limited to, a CPU.

The output module 423 is used for outputting the respective width of the respiratory tract and displaying the ultrasound image. The ultrasound image has the region of interest, the respective airspace region and a non-airspace region. In one embodiment, the output module 423 is a signal output terminal of the first computing device 420 and wiredly or wirelessly connected to a storage device or an output interface. For example, the output module 423 is, but not limited to, a touch screen.

The second computing device 430 is coupled to the first computing device 420, for calculating a second statistic value of the widths of the respiratory tract. The identifying device 440 is coupled to the second computing device 430. Moreover, the identifying device 440 is adapted to classify the status about an airway obstruction in the subject.

In one embodiment, the system further comprises a determining device (not shown in figures). The determining device is coupled to the identifying device 440. When the second statistic value and a third statistic value are calculated and obtained by measuring the width of the respiratory tracts, the determining device is adapted to determine whether the subject has an airway obstruction by comparing the second statistic value and the third statistic value which are calculated by the second computing device. For example, compared values are obtained by comparing the second statistic value and the third statistic value (e.g. subtracting or dividing those two values) to confirm if the subject has an airway obstruction.

In prior art, there is no accurate method of diagnosing the airway obstruction. Therefore, the disclosure provides the computer-implemented method for determining the width of the respiratory tract and system thereof. Since the width of the respiratory tract is determined according to the quantitative analysis of the ultrasound image, the manual error can be reduced. Additionally, the disclosure provides the method for diagnosing airway obstruction based on the width of the respiratory tract, and comparing the different statistic values to determine whether the subject has an airway obstruction or not.

It is believed that a person of ordinary knowledge in the art can utilize the present invention to its broadest scope based on the descriptions herein with no need of further illustration. Therefore, the descriptions and claims only serve as an illustration, instead of limitation of the present invention.

We claim:

1. A system for determining a width of a respiratory tract, comprising:
    an ultrasound imaging device for collecting an ultrasound image of a region of the respiratory tract, the ultrasound image having a plurality of pixels, and each pixel having a color scale value; and
    a computing device coupled to the ultrasound imaging device, comprising:
        an input module for receiving the ultrasound image, allowing a user to select a region of interest, and calculating a first statistic value of color scale value of the pixels therein;
        a classifier module for identifying pixels in the region of interest which have a color scale value larger than or equal to the first statistic value to define an airspace region, and for calculating a width of the respiratory tract based on the distribution of the pixels in the airspace region; and
        an output module for outputting the width of the respiratory tract and displaying the ultrasound image.

2. The system of claim 1, wherein the ultrasound imaging device is a 2D ultrasonic probe or a 3D ultrasonic probe, and the ultrasound image is obtained by parallel scanning, fan-like scanning, or free-surface scanning.

3. A system adapted to diagnose airway obstruction in a subject, comprising:
    an ultrasound imaging device for obtaining an ultrasound image of a region of the respiratory tract, the ultrasound image having a plurality of pixels, and each pixel having a color scale value;
    a first computing device coupled to the ultrasound imaging device, comprising:
        an input module for receiving the ultrasound image, allowing a user to select a region of interest, and calculating a first statistic value of color scale value of the pixels therein;
        a classifier module for identifying pixels in the region of interest which have a color scale value larger than or equal to the first statistic value to define an airspace region, and for calculating a width of the respiratory tract based on the distribution of the pixels in the airspace region; and an output module for outputting the width of the respiratory tract and displaying the ultrasound image;

a second computing device coupled to the first computing device, for calculating a second statistic value of the widths of the respiratory tract; and an identifying device coupled to the second computing device and adapted to classify the status about an airway obstruction in the subject.

4. The system of claim 3, wherein the ultrasound imaging device is a 2D ultrasonic probe or a 3D ultrasonic probe, and the ultrasound image is obtained by parallel scanning, fan-like scanning, or free-surface scanning.

5. The system of claim 3, further comprising a determining device coupled to the identifying device, for determining whether the subject has an airway obstruction by comparing the second statistic value and a third statistic value which are calculated by the second computing device.

* * * * *